US012603164B2

(12) United States Patent
Sekiguchi

(10) Patent No.: US 12,603,164 B2

(45) Date of Patent: Apr. 14, 2026

(54) CONTROL APPARATUS, METHOD FOR DISPLAYING DATA LOGS AND MEDICAL CENTRALIZED CONTROL SYSTEM

(71) Applicant: OLYMPUS CORPORATION, Tokyo (JP)

(72) Inventor: Kiyoshi Sekiguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 95 days.

(21) Appl. No.: 18/085,920

(22) Filed: Dec. 21, 2022

(65) Prior Publication Data

US 2023/0125596 A1    Apr. 27, 2023

Related U.S. Application Data

(63) Continuation of application No. PCT/JP2020/027819, filed on Jul. 17, 2020.

(51) Int. Cl.
| | |
|---|---|
| *G16H 30/20* | (2018.01) |
| *G06F 11/00* | (2006.01) |
| *G16H 15/00* | (2018.01) |
| *G16H 30/40* | (2018.01) |
| *G16H 40/63* | (2018.01) |

(52) U.S. Cl.
CPC ............. *G16H 15/00* (2018.01); *G16H 40/63* (2018.01)

(58) Field of Classification Search
CPC ........ G16H 15/00; G16H 40/63; G16H 40/20; G16H 20/40
See application file for complete search history.

(56) References Cited

U.S. PATENT DOCUMENTS

| | | | | |
|---|---|---|---|---|
| 2018/0158545 A1* | 6/2018 | Blomquist | ............. | G16H 20/13 |
| 2018/0369039 A1* | 12/2018 | Bhimavarapu | ........ | A61G 7/018 |
| 2020/0058384 A1* | 2/2020 | Sugai | ..................... | G16H 40/20 |
| 2023/0210579 A1* | 7/2023 | Torabi | ................... | G16H 40/40 |

FOREIGN PATENT DOCUMENTS

| | | |
|---|---|---|
| JP | 2003-070748 A | 3/2003 |
| JP | 2011-043962 A | 3/2011 |
| JP | 2015-087875 A | 5/2015 |
| JP | 2019-076246 A | 5/2019 |
| WO | 2019/116628 A1 | 6/2019 |

OTHER PUBLICATIONS

International Search Report dated Oct. 13, 2020 received in PCT/JP2020/027819.

* cited by examiner

*Primary Examiner* — Maroun P Kanaan

(74) *Attorney, Agent, or Firm* — Scully, Scott, Murphy & Presser, P.C.

(57) ABSTRACT

A control apparatus includes a processor, and the processor receives data logs related to operations of a plurality of controlled devices, adds, based on information on a predetermined person in charge of surgery set according to the data logs, information on the person in charge of surgery according to the plurality of controlled devices to the data logs related to the operations of the plurality of controlled devices obtained from results of communication with the plurality of controlled devices, and extracts data logs for each predetermined person in charge of surgery from the data logs and the information on the set person in charge of surgery.

15 Claims, 14 Drawing Sheets

TBL1

| TYPE OF OPERATION LOG | PERSON IN CHARGE OF SURGERY |
|---|---|
| ELECTRIC KNIFE OUTPUT | SURGEON |
| WHITE BALANCE | SCOPIST |
| ZOOM UP/DOWN | SCOPIST |
| PATIENT MEDICAL CHART INPUT | NURSE IN NON-STERILE AREA |
| RECORDING START/STOP | NURSE IN NON-STERILE AREA |
| ⋮ | ⋮ |

FIG. 4

| OCCURRENCE TIME | TYPE OF OPERATION LOG | PERSON IN CHARGE OF SURGERY |
|---|---|---|
| 10:35:00 | PATIENT MEDICAL CHART INPUT | NURSE IN NON-STERILE AREA |
| 10:35:11 | WHITE BALANCE | SCOPIST |
| 10:37:23 | RECORDING START | NURSE IN NON-STERILE AREA |
| 10:38:00 | ELECTRIC KNIFE OUTPUT | SURGEON |
| 10:38:15 | ZOOM UP | SCOPIST |
| 10:38:16 | ZOOM UP | SCOPIST |
| 10:38:17 | ZOOM DOWN | SCOPIST |
| 10:40:11 | ELECTRIC KNIFE OUTPUT | SURGEON |
| 10:40:12 | ELECTRIC KNIFE OUTPUT | SURGEON |
| 10:40:13 | ELECTRIC KNIFE OUTPUT | SURGEON |
| 10:40:14 | ELECTRIC KNIFE OUTPUT | SURGEON |
| ⋮ | ⋮ | ⋮ |
| 14:20:22 | RECORDING STOP | NURSE IN NON-STERILE AREA |

FIG. 5A

| OCCURRENCE TIME | TYPE OF OPERATION LOG | PERSON IN CHARGE OF SURGERY |
|---|---|---|
| 10:35:11 | WHITE BALANCE | SCOPIST |
| 10:38:15 | ZOOM UP | SCOPIST |
| 10:38:16 | ZOOM UP | SCOPIST |
| 10:38:17 | ZOOM DOWN | SCOPIST |

FIG. 5B

| OCCURRENCE TIME | TYPE OF OPERATION LOG | PERSON IN CHARGE OF SURGERY |
|---|---|---|
| 10:38:00 | ELECTRIC KNIFE OUTPUT | SURGEON |
| 10:40:11 | ELECTRIC KNIFE OUTPUT | SURGEON |
| 10:40:12 | ELECTRIC KNIFE OUTPUT | SURGEON |
| 10:40:13 | ELECTRIC KNIFE OUTPUT | SURGEON |
| 10:40:14 | ELECTRIC KNIFE OUTPUT | SURGEON |

FIG. 5C

| OCCURRENCE TIME | TYPE OF OPERATION LOG | PERSON IN CHARGE OF SURGERY |
|---|---|---|
| 10:35:00 | PATIENT MEDICAL CHART INPUT | NURSE IN NON-STERILE AREA |
| 10:37:23 | RECORDING START | NURSE IN NON-STERILE AREA |
| ⋮ | ⋮ | ⋮ |
| 14:20:22 | RECORDING STOP | NURSE IN NON-STERILE AREA |

FIG. 6

LOG DATA FOR EACH PERSON IN CHARGE OF SURGERY

| OCCURRENCE TIME | TYPE OF OPERATION LOG | PERSON IN CHARGE OF SURGERY |
|---|---|---|
| 10:35:11 | WHITE BALANCE | SCOPIST |
| 10:38:15 | ZOOM UP | SCOPIST |
| 10:38:16 | ZOOM UP | SCOPIST |
| 10:38:17 | ZOOM DOWN | SCOPIST |

MODEL LOG DATA (ACQUIRED FROM SERVER/CLOUD)

| OCCURRENCE TIME | TYPE OF OPERATION LOG | PERSON IN CHARGE OF SURGERY |
|---|---|---|
| xx:yy:zz | WHITE BALANCE | SCOPIST |
| xv:vz:zx | ZOOM UP | SCOPIST |
| | | |
| | | |

FIG. 10

TBL2

| TYPE OF OPERATION LOG | PERSON IN CHARGE OF SURGERY |
|---|---|
| ELECTRIC KNIFE OUTPUT | SURGEON (STERILE AREA) |
| WHITE BALANCE | SCOPIST (STERILE AREA) |
| ZOOM UP/DOWN | SCOPIST (STERILE AREA) |
| PATIENT MEDICAL CHART INPUT | NURSE IN NON-STERILE AREA (NON-STERILE AREA) |
| RECORDING START/STOP | NURSE IN NON-STERILE AREA (NON-STERILE AREA) |
| ⋮ | ⋮ |

FIG. 11

| OCCURRENCE TIME | TYPE OF OPERATION LOG | PERSON IN CHARGE OF SURGERY |
|---|---|---|
| 10:34:55 | USER AUTHENTICATION (OPERATION START) | SURGEON A, SCOPIST A |
| 10:35:00 | PATIENT MEDICAL CHART INPUT | NURSE B IN NON-STERILE AREA |
| 10:35:11 | WHITE BALANCE | SCOPIST A |
| 10:37:23 | RECORDING START | NURSE A IN NON-STERILE AREA |
| 10:38:00 | ELECTRIC KNIFE OUTPUT | SURGEON A |
| 10:38:15 | ZOOM UP | SCOPIST A |
| 10:38:16 | ZOOM UP | SCOPIST A |
| 10:38:17 | ZOOM DOWN | SCOPIST A |
| 10:40:11 | ELECTRIC KNIFE OUTPUT | SURGEON A |
| 10:40:12 | ELECTRIC KNIFE OUTPUT | SURGEON A |
| 10:40:13 | ELECTRIC KNIFE OUTPUT | SURGEON A |
| 10:40:14 | ELECTRIC KNIFE OUTPUT | SURGEON A |
| ⋮ | ⋮ | ⋮ |
| 14:20:22 | RECORDING STOP | NURSE B IN NON-STERILE AREA |
| ⋮ | ⋮ | ⋮ |

| OCCURRENCE TIME | TYPE OF OPERATION LOG |
|---|---|
| 10:34:55 | USER AUTHENTICATION (SURGERY START) |
| 10:35:00 | PATIENT MEDICAL CHART INPUT |
| 10:35:11 | WHITE BALANCE |
| 10:37:23 | RECORDING START |
| 10:38:00 | ELECTRIC KNIFE OUTPUT |
| 10:38:15 | ZOOM UP |
| 10:38:16 | ZOOM UP |
| 10:38:17 | ZOOM DOWN |
| 10:40:11 | ELECTRIC KNIFE OUTPUT |
| 10:40:12 | ELECTRIC KNIFE OUTPUT |
| 10:40:13 | ELECTRIC KNIFE OUTPUT |
| 10:40:14 | ELECTRIC KNIFE OUTPUT |
| ... | ... |
| 14:20:22 | RECORDING STOP |
| ... | ... |

FIG. 14A

| OCCURRENCE TIME | TYPE OF OPERATION LOG | PERSON IN CHARGE OF SURGERY | |
|---|---|---|---|
| 10:35:11 | WHITE BALANCE | SCOPIST | DISPLAY SCOPIST'S LINE-OF-SIGHT CAMERA VIDEO AND ENDOSCOPE VIDEO TOGETHER |
| 10:38:15 | ZOOM UP | SCOPIST | |
| 10:38:16 | ZOOM UP | SCOPIST | |
| 10:38:17 | ZOOM DOWN | SCOPIST | |

FIG. 14B

| OCCURRENCE TIME | TYPE OF OPERATION LOG | PERSON IN CHARGE OF SURGERY | |
|---|---|---|---|
| 10:38:00 | ELECTRIC KNIFE OUTPUT | SURGEON | DISPLAY SURGEON'S LINE-OF-SIGHT CAMERA VIDEO AND ENDOSCOPE VIDEO TOGETHER |
| 10:40:11 | ELECTRIC KNIFE OUTPUT | SURGEON | |
| 10:40:12 | ELECTRIC KNIFE OUTPUT | SURGEON | |
| 10:40:13 | ELECTRIC KNIFE OUTPUT | SURGEON | |
| 10:40:14 | ELECTRIC KNIFE OUTPUT | SURGEON | |

FIG. 14C

| OCCURRENCE TIME | TYPE OF OPERATION LOG | PERSON IN CHARGE OF SURGERY | |
|---|---|---|---|
| 10:35:00 | PATIENT MEDICAL CHART INPUT | NURSE IN NON-STERILE AREA | DISPLAY LINE-OF-SIGHT CAMERA VIDEO OF NURSE IN NON-STERILE AREA |
| 10:37:23 | RECORDING START | NURSE IN NON-STERILE AREA | |
| ⋮ | ⋮ | ⋮ | |
| 14:20:22 | RECORDING STOP | NURSE IN NON-STERILE AREA | |

FIG. 15

LOG DATA + VIDEO FOR EACH PERSON IN CHARGE OF SURGERY

| OCCURRENCE TIME | TYPE OF OPERATION LOG | PERSON IN CHARGE OF SURGERY | |
|---|---|---|---|
| 10:35:11 | WHITE BALANCE | SCOPIST | |
| 10:38:15 | ZOOM UP | SCOPIST | DISPLAY SCOPIST'S LINE-OF-SIGHT CAMERA |
| 10:38:16 | ZOOM UP | SCOPIST | VIDEO AND ENDOSCOPE VIDEO TOGETHER |
| 10:38:17 | ZOOM DOWN | SCOPIST | |

MODEL LOG DATA + MODEL VIDEO (ACQUIRED FROM SERVER/CLOUD)

| OCCURRENCE TIME | TYPE OF OPERATION LOG | PERSON IN CHARGE OF SURGERY | |
|---|---|---|---|
| xx:yy:zz | WHITE BALANCE | SCOPIST | DISPLAY SCOPIST'S MODEL LINE-OF-SIGHT CAMERA |
| xy:yz:zx | ZOOM UP | SCOPIST | VIDEO AND ENDOSCOPE VIDEO TOGETHER |
| | | | |

CONTROL APPARATUS, METHOD FOR DISPLAYING DATA LOGS AND MEDICAL CENTRALIZED CONTROL SYSTEM

CROSS REFERENCE TO RELATED APPLICATION

This application is a continuation application of PCT/JP2020/027819 filed on Jul. 17, 2020, the entire contents of which are incorporated herein by this reference.

BACKGROUND OF THE INVENTION

1. Field of the Invention

The present invention relates to a control apparatus, a method for displaying data logs, and a medical centralized control system, and more particularly, to a control apparatus configured to control a plurality of controlled devices, a method for displaying data logs, and a medical centralized control system.

2. Description of the Related Art

Conventionally, operating rooms have been provided with various medical devices and various non-medical devices. These various devices include devices such as shadowless lamps, endoscope apparatuses and insufflation apparatuses. A system controller as a centralized control apparatus communicates with such various devices, sets set values for the various devices and performs centralized control.

When an operation panel apparatus is connected to the system controller and surgery starts, a person in charge of the surgery such as a surgeon, a scopist, and a nurse can give execution instructions, and set or change various set values for a desired device by operating the operation panel apparatus.

Operation for each device includes giving an instruction to execute or stop a function of the device, making settings related to the functions, and the like, and a person in charge of surgery such as a surgeon, a scopist, or a nurse operates each device directly or causes an operation screen to be displayed on the operation panel apparatus and performs a desired operation.

The person in charge of surgery reviews log data such as operation logs related to operation of each device during the surgery or error logs related to errors that have occurred and looks back at actions during the surgery, and can thereby improve skills. The log data related to operation of each device or errors that have occurred can be saved and displayed by the system controller as a centralized control apparatus configured to communicate with each device. For example, Japanese Patent Application Laid-Open Publication No. 2019-76246 discloses a medical control apparatus configured to collect log data such as operation of each device during surgery or errors that have occurred.

SUMMARY OF THE INVENTION

A centralized control apparatus according to an aspect of the present invention includes a processor, and the processor receives data logs related to operations of a plurality of controlled devices, adds, based on information on a predetermined person in charge of surgery set according to the data logs, information on the person in charge of surgery according to the plurality of controlled devices to the data logs related to the operations of the plurality of controlled devices obtained from results of communication with the plurality of controlled devices, and extracts data logs for each predetermined person in charge of surgery from the data logs and the information on the set person in charge of surgery.

A method for displaying data logs according to an aspect of the present invention includes receiving data logs related to operations of a plurality of controlled devices, setting information on a person in charge of surgery according to the data logs, adding the information on the person in charge of surgery according to the plurality of controlled devices to the data logs related to the operations of the plurality of controlled devices obtained from results of communication with the plurality of controlled devices, and extracting the data logs for each predetermined person in charge of surgery from the data logs and the information on the set person in charge of surgery and displaying the data logs.

A medical centralized control system according to an aspect of the present invention includes a plurality of controlled devices and a control apparatus including a processor and configured to centrally control the plurality of controlled devices. The processor communicates with the plurality of controlled devices, sets information on a person in charge of surgery according to the plurality of controlled devices, adds the information on the person in charge of surgery according to the plurality of controlled devices to data logs related to operations of the plurality of controlled devices obtained from results of communication with the plurality of controlled devices and records the data logs, and extracts data logs for each predetermined person in charge of surgery from the recorded data logs and the information on the set person in charge of surgery.

BRIEF DESCRIPTION OF THE DRAWINGS

FIG. 2 is a block diagram illustrating a configuration of a system controller;

FIG. 3 is a diagram illustrating an example of a table in which a type of an operation log is associated with a person in charge of surgery;

FIG. 4 is a diagram illustrating an example of log data stored in a history information storage unit;

FIG. 5A is a diagram illustrating an example of a display screen when a person in charge of surgery extracts log data of a scopist;

FIG. 5B is a diagram illustrating an example of a display screen when a person in charge of surgery extracts log data of a surgeon;

FIG. 5C is a diagram illustrating an example of a display screen when a person in charge of surgery extracts log data of a nurse in a non-sterile area;

FIG. 6 is a diagram illustrating an example in which log data for each person in charge of surgery obtained during surgery is compared with model log data;

FIG. 10 is a diagram illustrating an example of a table in which a type of operation log is associated with the person in charge of surgery;

FIG. 11 is a diagram illustrating an example of operation log information stored in a history information storage unit;

FIG. 14A is a diagram illustrating an example of a display screen when a person in charge of surgery extracts log data of a scopist;

FIG. 14B is a diagram illustrating an example of a display screen when a person in charge of surgery extracts log data of a surgeon;

FIG. 14C is a diagram illustrating an example of a display screen when a person in charge of surgery extracts log data of a nurse in the non-sterile area;

FIG. 15 is a diagram illustrating an example in which log data and video for each person in charge of surgery obtained during surgery are compared with model log data and model video.

DETAILED DESCRIPTION OF THE PREFERRED EMBODIMENTS

Hereinafter, embodiments of the present invention will be described using the attached drawings.

First Embodiment (Configuration of Operation System)

Figure 1:
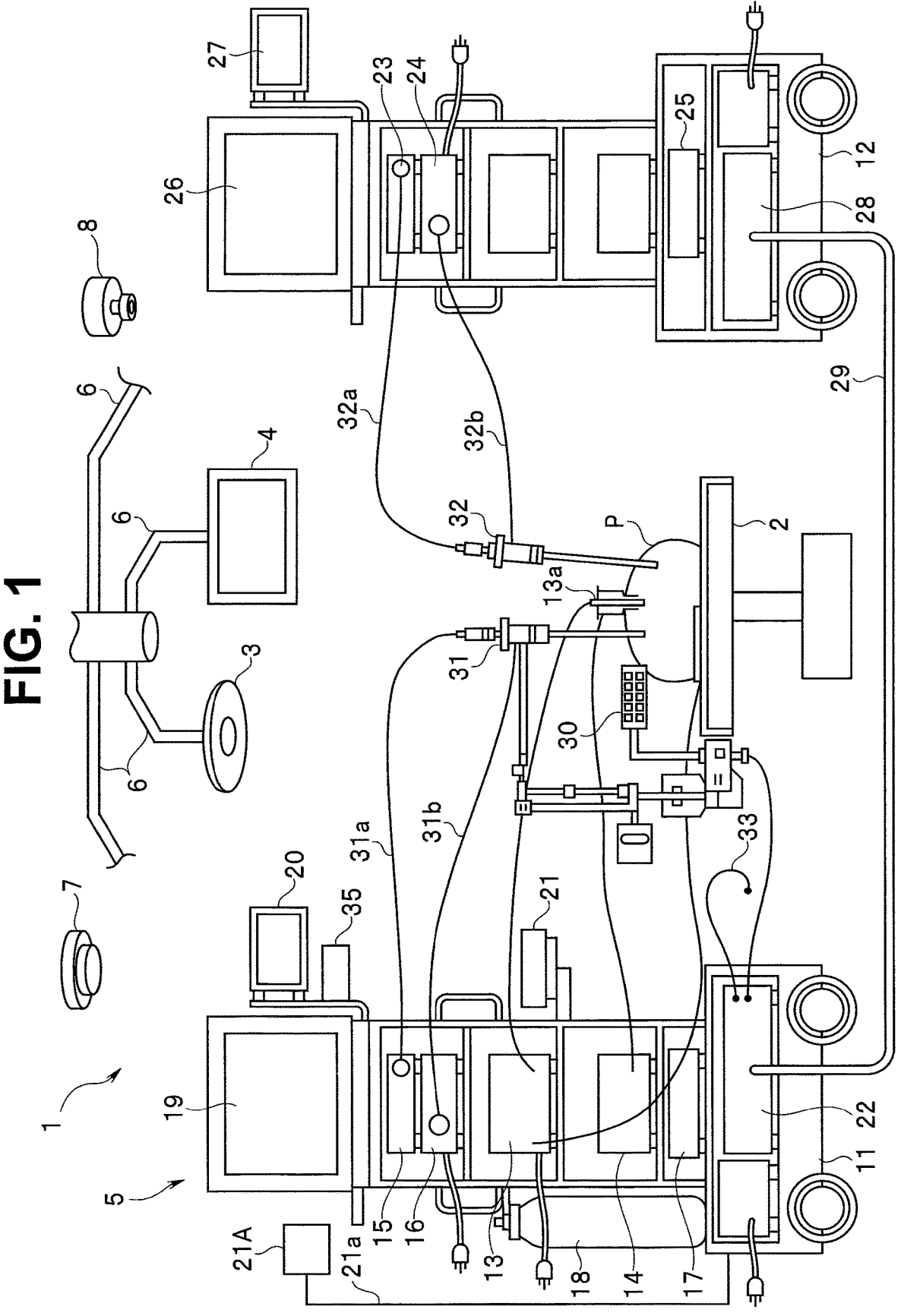
FIG. 1 is a configuration diagram illustrating a configuration of an operation system according to a first embodiment of the present invention.

First, an overall configuration of an operation system disposed in an operating room will be described using FIG. 1. FIG. 1 is a configuration diagram illustrating a configuration of an operation system according to a first embodiment of the present invention. The operation system includes a plurality of medical devices such as an endoscope and a plurality of non-medical devices such as a shadowless lamp.

As shown in FIG. 1, an operating table 2 on which a patient P lies, a plurality of shadowless lamps 3, a display apparatus 4 and a medical system 5 are disposed in an operating room. The medical system 5 includes a first cart 11 and a second cart 12. Each shadowless lamp 3 and display apparatus 4 are fixed to a ceiling of the operating room by arms 6. Furthermore, an interior light 7 is installed on the ceiling in the operating room. A surgical field camera 8 and a room camera (not shown) are also installed in the operating room.

The first cart 11 is provided with apparatuses such as an electric knife apparatus 13, an insufflation apparatus 14, a video processor 15, a light source apparatus 16 and a recorder 17 for recording as medical devices, which are controlled apparatuses, and a gas cylinder 18 filled with carbon dioxide. The video processor 15 is connected to a first endoscope 31 via a camera cable 31a.

The light source apparatus 16 is connected to the first endoscope 31 via a light guide cable 31b. A display apparatus 19, a first centralized display panel 20, an operation panel apparatus 21 or the like are mounted on the first cart 11. The display apparatus 19 is, for example, a TV monitor that displays endoscope images or the like.

The recorder 17 is a recording apparatus including a mass storage such as a hard disk drive apparatus.

The centralized display panel 20 constitutes display means capable of selectively displaying all data during surgery. The operation panel apparatus 21 is constructed of, for example, a display unit such as a liquid crystal display and a touch panel integrally provided on the display unit, and constitutes a centralized operation apparatus operated by a nurse or the like in a non-sterile area.

Furthermore, a system controller 22, which is a centralized control apparatus, is mounted on the first cart 11. The shadowless lamps 3, the interior light 7, the electric knife apparatus 13, the insufflation apparatus 14, the video processor 15, the light source apparatus 16, the recorder 17 or the like, which are described above, are connected to the system controller 22 via a communication line (not shown). Moreover, a headset type microphone 33 can be connected to the system controller 22 and the system controller 22 can recognize voice inputted from the microphone 33 and control each device by an operator's voice.

A second operation panel apparatus 21A installed on a wall of the operating room is also connected to the system controller 22 via a cable 21a, and the nurse or the like in the non-sterile area can also perform operation on each device through the operation panel apparatus 21A.

The first cart 11 is provided with the first endoscope 31 and an RFID (radio frequency identification) terminal 35 that can wirelessly read/write individual ID information using an ID tag embedded in a treatment instrument 13a or the like connected to the electric knife apparatus 13.

On the other hand, a video processor 23, a light source apparatus 24, an image processing apparatus 25, a display apparatus 26 and a centralized display panel 27, which are controlled apparatuses, are mounted on the second cart 12. The video processor 23 is connected to a second endoscope 32 via a camera cable 32a. The light source apparatus 24 is connected to the second endoscope 32 via a light guide cable 32b.

The display apparatus 26 displays an endoscope image or the like captured by the video processor 23. The centralized display panel 27 can selectively display all data during surgery.

The video processor 23, the light source apparatus 24 and the image processing apparatus 25 or the like are connected to a relay unit 28 mounted on the second cart 12 via a communication line (not shown). The relay unit 28 is connected to the system controller 22 mounted on the above-described first cart 11 via a relay cable 29.

In this way, the system controller 22 can perform centralized control on the video processor 23, the light source apparatus 24 and the image processing apparatus 25, mounted on the second cart 12, and the electric knife apparatus 13, the insufflation apparatus 14, the video processor 15, the light source apparatus 16 and the recorder 17, mounted on the first cart 11, and each shadowless lamp 3, each display apparatus 4 and the interior light 7.

Therefore, when communication is in progress between the system controller 22 and these apparatuses, the system controller 22 can display setting conditions of the connected apparatuses and setting screens of operation switches or the like on liquid crystal displays of the above-described operation panel apparatuses 21 and 21A. Furthermore, when a desired operation switch is touched and a touch panel in a predetermined region is operated, the system controller 22 can perform operation and input such as set value changes.

A remote controller 30 is a second centralized operation apparatus operated by a surgeon or the like in a sterile area, and can operate other apparatuses with which communication is established via the system controller 22.

Furthermore, the system controller 22 is provided with an infrared communication port (not shown), which is communication means. The infrared communication port is provided at a position, for example, in the vicinity of the display apparatus 19 from where infrared rays can be easily radiated, and the infrared communication port and the system controller 22 are connected via a cable.

(Configuration of System Controller)

Figure 2:
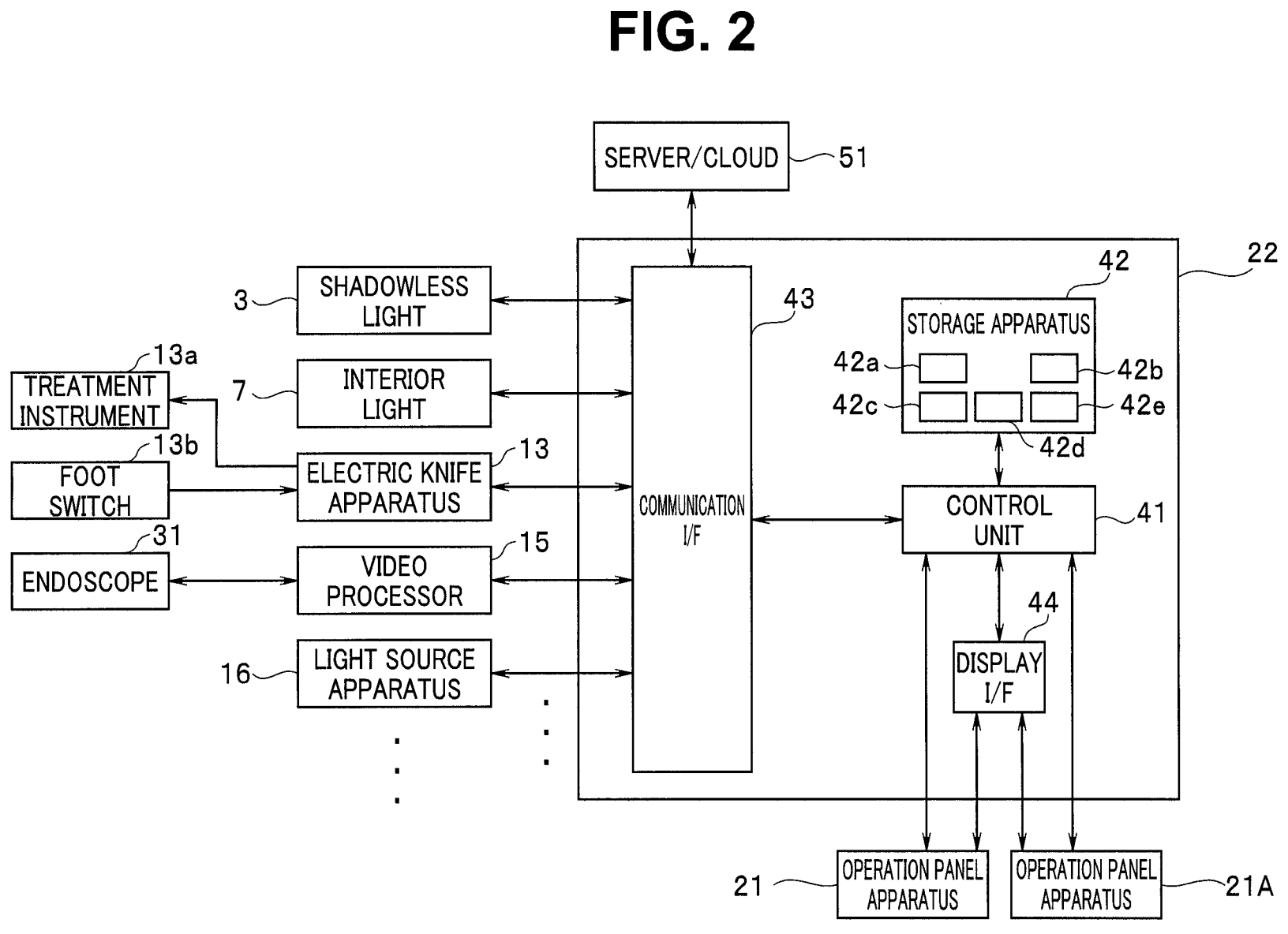

FIG. 2 is a block diagram illustrating a configuration of the system controller.

The system controller 22 includes a control unit 41, a storage apparatus 42, a communication interface (hereinafter abbreviated as a "communication I/F") 43 and a display interface (hereinafter abbreviated as a "display I/F") 44.

The control unit 41 can be configured as a processor equipped with a central processing unit (hereinafter referred to as a "CPU"), a ROM, a RAM or the like, and various functions of the system controller 22 are implemented with the CPU reading and executing software programs of various functions recorded in the ROM. The processor may implement a function of each section by separate pieces of hardware or implement part of each section by a single integral piece of hardware. For example, the processor may include hardware and the hardware may include at least one of a circuit for processing digital signals or a circuit for processing analog signals. The processor can use various processors such as a DSP (digital signal processor) other than the central processing unit (CPU). Furthermore, the processor may also be a hardware circuit using an ASIC (application specific integrated circuit) or an FPGA (field programmable gate array).

The storage apparatus 42 is a non-volatile, rewritable storage apparatus such as a flash memory or a hard disk apparatus. The storage apparatus 42 also stores software programs for various functions of the system controller 22 and the CPU of the control unit 41 can read and execute the software programs.

The storage apparatus 42 includes a program storage unit 42*a* configured to store software programs for various functions including a program for recording log data, which will be described later.

The software programs stored in the program storage unit 42*a* include, in addition to the control program to control operations of various devices included in the operation system 1, a batch setting processing program to make batch device settings for each scene, a screen generating program to generate various screens such as an operation screen for a specified function, a history information recording program to record log data such as operation logs and error logs.

The storage apparatus 42 includes a setting information storage unit 42*b* to store various setting information on a plurality of devices for each scene. The setting information storage unit 42*b* includes set values set in advance for each device to be used in various scenes by a person in charge of surgery.

More specifically, the setting information storage unit 42*b* stores for each scene, information (hereinafter also referred to as "setting information") on one or two or more devices used in the scene. Examples of set values include on/off, output values or thresholds of each device.

When the person in charge of surgery selects a scene, the control unit 41 executes a batch setting processing program configured to read setting information on each device about the selected scene from the setting information storage unit 42*b* and set the setting information in a plurality of corresponding devices.

Furthermore, the storage apparatus 42 includes a history information storage unit 42*c* as a data log recording unit configured to store operation information (operation logs) on operations carried out by the person in charge of surgery on one or two or more controlled devices as log data.

The person in charge of surgery selects a scene and performs surgery while operating, desired devices, for example, the treatment instrument 13*a* such as an electric knife connected to the electric knife apparatus 13, the endoscope 31 or 32. The treatment instrument 13*a* is turned on/off by a foot switch 13*b* connected to the electric knife apparatus 13. The history information storage unit 42*c* stores history information on the operation performed by the person in charge of surgery as log data.

Furthermore, the storage apparatus 42 includes an error information storage unit 42*d* configured to store error information (error logs) about various errors occurred in the batch settings and operations of various devices as log data.

The storage apparatus 42 includes a table holding unit 42*e* configured to store a table, which will be described later and in which the type of log data is associated with the person in charge of surgery.

The communication I/F 43 as the device communication interface unit to which a plurality of communication lines connected to the plurality of devices are connected is an interface circuit for the control unit 41 to communicate with each device. Among the plurality of devices, the shadowless light 3, the interior light 7, the electric knife apparatus 13, the video processor 15, the light source apparatus 16 and the server/cloud 51 are shown in FIG. 2. Therefore, the control unit 41 can turn on/off each device, set or change set values, acquire log data such as operation information or error information from each device and the like by communicating with each device via the communication I/F 43.

Furthermore, the control unit 41 receives operation signals from the operation panel apparatuses 21 and 21A and outputs image signals of the display screens to be displayed on the liquid crystal displays of the operation panel apparatuses 21 and 21A to the operation panel apparatuses 21 and 21A via the display I/F 44.

The person in charge of surgery can instruct to execute an operation of each device on the display screen of the operation panel apparatus 21 or 21A or receive operation information, error information or the like when operating each device on the display screen.

These operations performed and errors made by the person in charge of surgery on the operation panel apparatus 21 or 21A are recorded as log data in the history information storage unit 42*c* and the error information storage unit 42*d* respectively.

(Operation)

Next, log data recording processing and log data extraction processing for each person in charge of surgery of the system controller 22 in the aforementioned operation system I will be described. Note that although the following description is given using operation logs as log data, error logs can also be subjected to the log data recording processing and the log data extraction processing for each person in charge of surgery in the like manner.

FIG. 3 is a diagram illustrating an example of a table in which each type of operation log is associated with each person in charge of surgery.

The table holding unit 42*e* of the storage apparatus 42 stores a table TBL1 as a person in charge of surgery setting unit in which each type of operation log is associated with each person in charge of surgery. As shown in FIG. 3, the types of operation logs include electric knife output, white balance, zoom UP/DOWN, patient medical chart input, recording start/stop or the like.

Examples of the person in charge of surgery include a surgeon, a scopist, a nurse in a non-sterile area, and each person in charge of surgery who performs the operation is associated with each type of operation log. The surgeon performs a procedure using the treatment instrument 13*a* such as an electric knife. The scopist causes an endoscope image to be displayed on the display apparatus 4 using the endoscope 31 or 32. The nurse in the non-sterile area inputs a patient medical chart or sets operation of each device using the operation panel apparatus 21 or 21A.

Therefore, the surgeon who performs the procedure using the treatment instrument 13*a* as the person in charge of surgery is associated with the electric knife output. The scopist who causes an endoscope image to be displayed using the endoscope 31 or 32 is associated with white balance and zoom UP/DOWN as the person in charge of surgery. Furthermore, the nurse in the non-sterile area who inputs a patient medical chart or sets operation of each device using the operation panel apparatus 21 or 21A is associated with patient medical chart input or recording start/stop as the person in charge of surgery.

Note that the table TBL1 can be edited based on control by the control unit 41. For example, a certain person in charge of surgery can edit the table TBL1 using a display screen displayed on the operation panel apparatus 21.

FIG. 4 is a diagram illustrating an example of log data stored in the history information storage unit.

When an operation log related to operation of each device is inputted, the control unit 41 records log data with the person in charge of surgery added in the history information storage unit 42*c* by referring to the table TBL1 in addition to an occurrence time and a type of operation log.

For example, when an operation log of patient medical chart input is inputted from the operation panel apparatus 21, the control unit 41 refers to the table TBL1 and determines that the person in charge of surgery is a nurse in the non-sterile area. The control unit 41 adds the person in charge of surgery determined by referring to the table TBL1 to time (that is, occurrence time) at which the operation log is inputted and the type of operation log and records the operation log in the history information storage unit 42*c*.

Similarly, when an operation log related to white balance is inputted, the control unit 41 refers to the table TBL1, adds the scopist as the person in charge of surgery and records the operation log. When an operation log of electric knife output is inputted, the control unit 41 refers to the table TBL1, adds a surgeon as the person in charge of surgery and records the operation log. In this way, as shown in FIG. 4, the log data in which the occurrence time, the type of operation log and the person in charge of surgery are associated with one another is recorded in the history information storage unit 42*c*.

The control unit 41 can extract log data for each person in charge of surgery from the log data recorded in the history information storage unit 42*c* and the table TBL1, and display the log data on the operation panel apparatus 21, for example. Thus, the control unit 41 as a data log extraction unit can extract log data for each person in charge of surgery from the log data recorded in the history information storage unit 42*c* and the table TBL1.

FIG. 5A is a diagram illustrating an example of a display screen when a person in charge of surgery extracts log data of a scopist, FIG. 5B is a diagram illustrating an example of a display screen when a person in charge of surgery extracts log data of a surgeon and FIG. 5C is a diagram illustrating an example of a display screen when a person in charge of surgery extracts log data of a nurse in a non-sterile area.

When the person in charge of surgery inputs information on the person in charge of surgery to be extracted using the operation panel apparatus 21, the control unit 41 extracts only the information on the person in charge of surgery inputted from the log data in FIG. 4. When the person in charge of surgery is, for example, a scopist, the control unit 41 displays only log data related to the scopist as shown in FIG. 5A. Similarly, when the person in charge of surgery is a surgeon, the control unit 41 displays only log data related to the surgeon as shown in FIG. 5B, and when the person in charge of surgery is a nurse in the non-sterile area as shown in FIG. 5C, the control unit 41 displays only log data related to the nurse in the non-sterile area. Thus, displaying only log data for each person in charge of surgery makes it easier to identify trends and problems of the person in charge of surgery.

For example, it is seen from FIG. 5A that zoom UP and DOWN are repeated from 10:38:15 to 10:38:17. This allows the scopist to find a point for improvement of, for example, "making practice so as to achieve an appropriate zoom magnification with less operation."

In FIG. 5B, electric knife output is performed consecutively from 10:40:11 to 10:40:13, and it is seen that the patient's burden increases. This allows the surgeon to find a point for improvement of, for example, "taking care so as to disperse electric knife output a little more."

It is seen in FIG. 5C that a patient medical chart is inputted from 10:35:00 to 10:37:23, which takes 2 minutes or more. This allows the nurse in the non-sterile area to find a point for improvement of, for example. "considering a little more efficient input method."

Furthermore, the control unit 41 can automatically generate a point for improvement (information on a point to be improved) for each person in charge of surgery. A server/cloud 51 stores model log data for each person in charge of surgery. The model log data is log data when a competent person in charge of surgery performs operation. The control unit 41 communicates with the server/cloud 51 via the communication I/F 43, acquires the model log data saved in the server/cloud 51, and compares log data for each person in charge of surgery obtained during surgery with the model log data.

FIG. 6 is a diagram illustrating an example in which log data for each person in charge of surgery obtained during surgery is compared with model log data. As shown in FIG. 6, the control unit 41 compares log data related to a scopist with model log data related to a scopist acquired from the server/cloud 51, and thereby automatically generates a point for improvement, for example, a message "taking time to adjust zooming." Thus, the control unit 41 as an improvement information presentation unit can present information on a point to be improved from the extracted log data for each person in charge of surgery.

Figure 7:
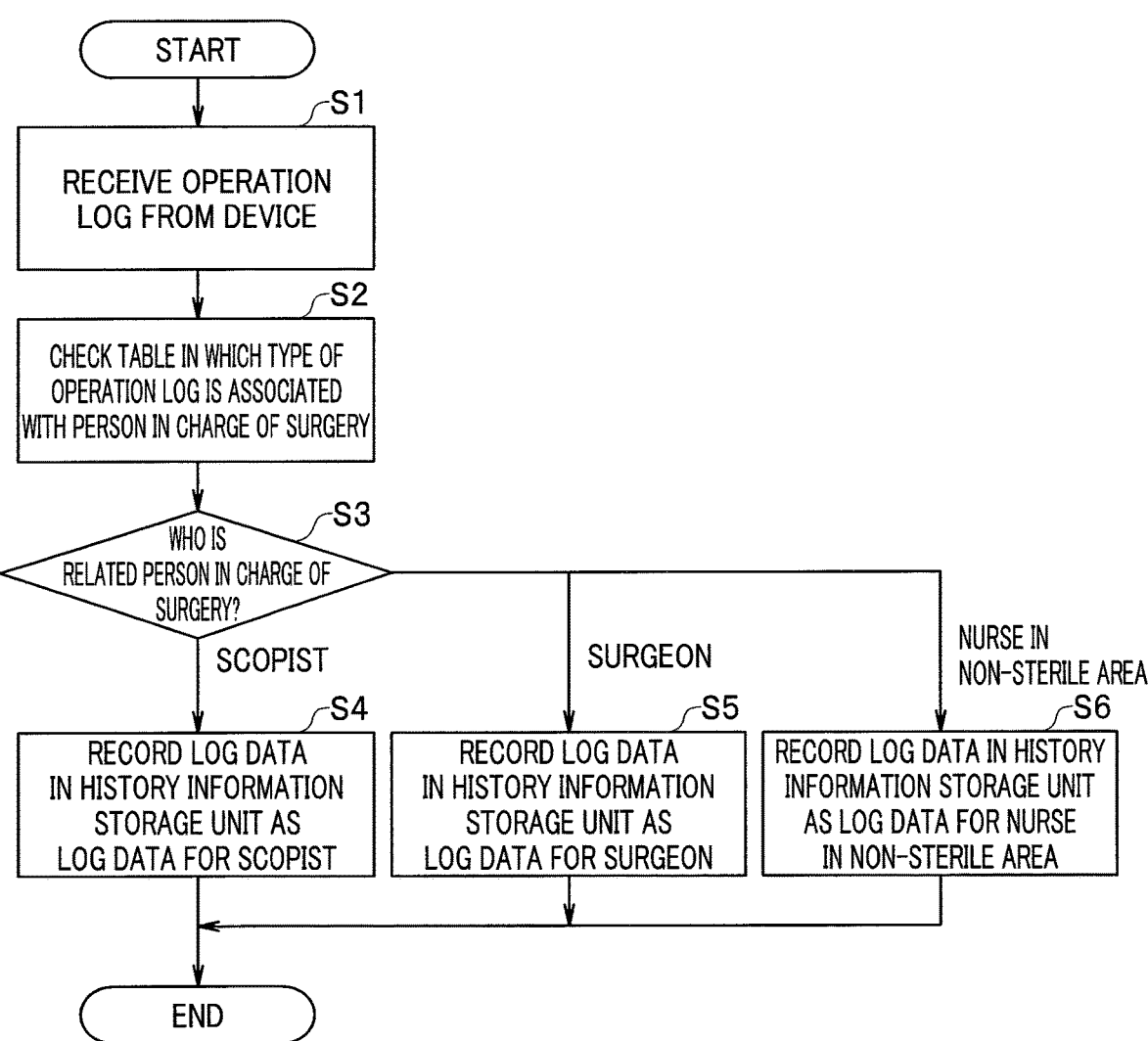
FIG. 7 is a flowchart illustrating an example of a flow of log data recording processing.

FIG. 7 is a flowchart illustrating an example of a flow of log data recording processing. Note that the processing in FIG. 7 is executed every time the control unit 41 receives an operation log from a device.

First, the control unit 41 receives an operation log related to an operation from the device (S1). The information on the operation log is inputted to the control unit 41 from the device via the communication I/F 43. Next, the control unit 41 checks the table TBL1 in which the type of operation log is associated with the person in charge of surgery (S2). The control unit 41 determines the person in charge of surgery related to the type of operation log (S3).

When the control unit 41 determines, as a result of the processing in S3, that the person in charge of surgery related to the type of operation log is a scopist, the control unit 41 records the operation log as log data for the scopist in the history information storage unit 42c (S4), and ends the processing. When the control unit 41 determines, as a result of the processing in S3, that the person in charge of surgery related to the type of operation log is a surgeon, the control unit 41 records the operation log as log data for the surgeon in the history information storage unit 42c (S5) and ends the processing. When the control unit 41 determines, as a result of the processing in S3, that the person in charge of surgery related to the type of operation log is a nurse in the non-sterile area, the control unit 41 records the operation log as log data for the nurse in the non-sterile area in the history information storage unit 42c (S6) and ends the processing.

Figure 8:
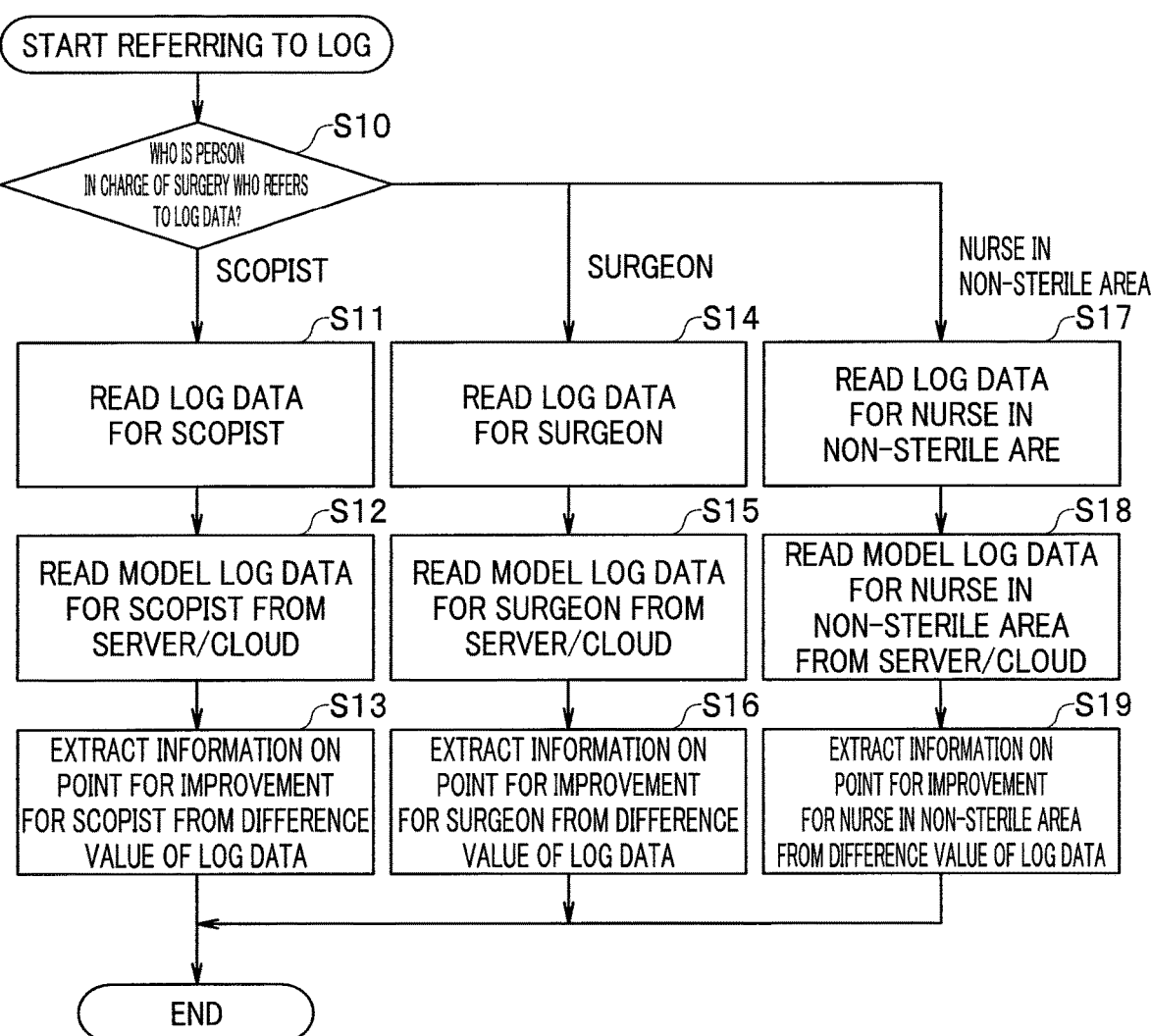
FIG. 8 is a flowchart illustrating an example of a flow of log data extraction processing for each person in charge of surgery.

FIG. 8 is a flowchart illustrating an example of a flow of log data extraction processing for each person in charge of surgery.

First, the control unit 41 determines a person in charge of surgery who refers to log data (S10). The person in charge of surgery such as a scopist, a surgeon or a nurse in the non-sterile area can set the person in charge of surgery who refers to log data using, for example, the operation panel apparatus 21.

When the control unit 41 determines, as a result of the processing in S10, that the person in charge of surgery who refers to the log data is a scopist, the control unit 41 reads the log data for the scopist from the log data of the history information storage unit 42c (S11). Next, the control unit 41 reads model log data for the scopist from the server/cloud 51 (S12). The control unit 41 extracts (generates) information on a point for improvement from a difference value of the log data (S13) and ends the processing.

When the control unit 41 determines, as a result of the processing in S10, that the person in charge of surgery who refers to the log data is a surgeon, the control unit 41 reads the log data for the surgeon from the log data of the history information storage unit 42c (S14). Next, the control unit 41 reads model log data for the surgeon from the server/cloud 51 (S15). The control unit 41 extracts (generates) information on a point for improvement from a difference value of the log data (S16) and ends the processing.

When the control unit 41 determines, as a result of the processing in S10, that the person in charge of surgery who refers to the log data is a nurse in the non-sterile area, the control unit 41 reads the log data for the nurse in the non-sterile area from the log data of the history information storage unit 42c (S17). Next, the control unit 41 reads model log data for the nurse in the non-sterile area from the server/cloud 51 (S18). The control unit 41 extracts (generates) information on a point for improvement from a difference value of the log data (S19) and ends the processing.

As described above, the control unit 41 of the system controller 22 refers to the table TBL1 in which the type of operation log is associated with the person in charge of surgery, adds which person in charge of surgery operates the operation log and records the operation log as log data. This allows the control unit 41 to extract only the log data related to the person in charge of surgery who wants to find a point for improvement from the log data. As a result, the person in charge of surgery (surgeon, scopist, nurse in the non-sterile area or the like) can see only the log data the person in charge of surgery wants to see, making it easier for the person in charge of surgery to review the person's own action, leading to skill improvement or the like.

Thus, according to the centralized control apparatus of the present embodiment, the person in charge of surgery can easily extract only log data related to the person's own operation.

Furthermore, the control unit 41 extracts only log data related to the person in charge of surgery who wants to find a point for improvement and compares the log data with model log data acquired from the server/cloud 51. This allows the control unit 41 to automatically extract a point for improvement from a difference value of the log data and the person in charge of surgery can more easily review the person's own action, which can lead to skill improvement or the like.

Second Embodiment

Next, a second embodiment will be described.

Figure 9:
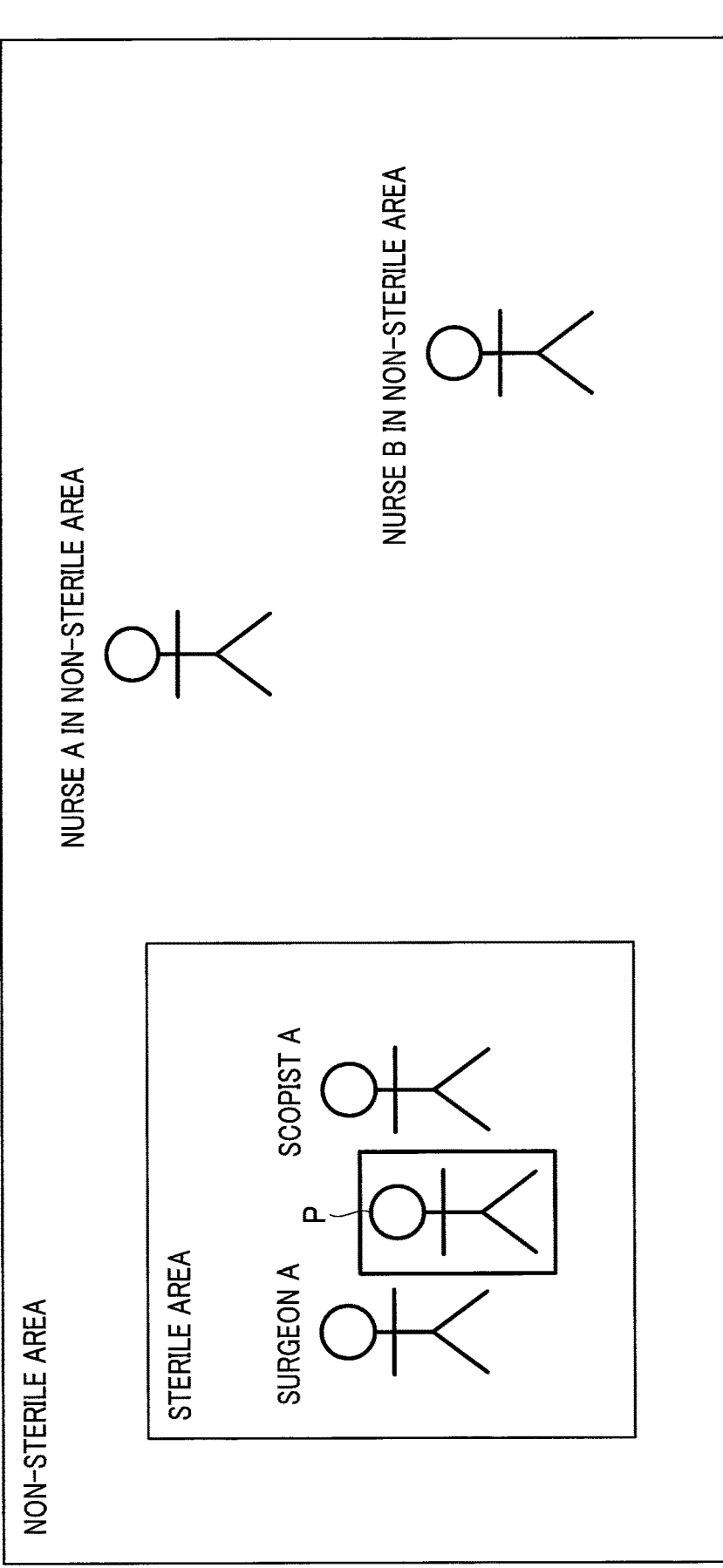
FIG. 9 is a diagram for schematically describing situations of a sterile area and the non-sterile area during surgery.

FIG. 9 is a diagram for schematically describing situations of the sterile area and the non-sterile area during surgery. As shown in FIG. 9, there is one patient P, one surgeon A who outputs the treatment instrument 13a such as an electric knife, and one scopist A who operates the endoscope 31 or 32 in the sterile area during surgery. Note that there may also be an assistant who operates forceps in the sterile area, but since the assistant only performs tasks that are not logged, the assistant is omitted in the illustration.

The scopist A does not perform operations performed by the surgeon A during surgery. Similarly, the surgeon A does not perform operations performed by the scopist A. Thus, it is possible to identify the operator without requiring user authentication of the surgeon A and the scopist A every time an operation is performed. In other words, the surgeon A and the scopist A need to perform user authentication only once at the start of surgery.

On the other hand, a plurality of nurses in the non-sterile area may participate in a surgery. As shown in FIG. 9, there are nurses A and B in the non-sterile area during the surgery. Thus, the nurses A and B in the non-sterile area cannot identify the operators without performing user authentication at each operation.

In other words, the surgeon A and the scopist A need to perform user authentication only once at the start of the surgery, whereas the nurses A and B in the non-sterile area have to perform user authentication at each operation before operating a certain device. Note that since the devices are not so often operated during surgery, performing user authentication is not troublesome even when user authentication has to be performed at each operation.

Thus, the person in charge of surgery (surgeon, scopist) in the sterile area performs user authentication only once at the start of surgery, whereas the person in charge of surgery in the non-sterile area (nurses in the non-sterile area) performs user authentication at each operation.

User authentication is performed by inputting information on the person in charge of surgery using the operation panel apparatus 21 as an authentication information input interface. Examples of methods of user authentication include authentication by user ID and password, and authentication by fingerprints. In the case of authentication by fingerprints, it is also possible to perform authentication using the fingerprints used when the operation panel apparatus 21 is operated.

FIG. 10 is a diagram illustrating an example of a table in which a type of operation log is associated with a person in charge of surgery. FIG. 11 is a diagram illustrating an example of operation log information stored in the history information storage unit.

The table holding unit 42*e* of the storage apparatus 42 stores a table TBL2 in which a type of operation log is associated with a person in charge of surgery as shown in FIG. 10. Although the table TBL2 is substantially the same as the table TBL1 in FIG. 3, information on whether the person in charge of surgery is in the sterile area or in the non-sterile area is added.

As shown in FIG. 11, the person in charge of surgery in the sterile area performs user authentication at the start of surgery. On the other hand, the person in charge of surgery in the non-sterile area performs user authentication at each operation. As a result, as shown in FIG. 11, an operation log is recorded with the person in charge of surgery who is user-authenticated when the operation is performed associated with the type of operation log. For example, the nurse B in the non-sterile area who is user-authenticated when the operation is performed is associated with an operation log of patient medical chart input and the nurse A in the non-sterile area who is user-authenticated when the operation is performed is associated with an operation log of recording start. Thus, the control unit as a person-in-charge-of-surgery identification unit adds information on the user authentication inputted from the operation panel apparatus 21 to the log data and records the log data.

Figure 12:
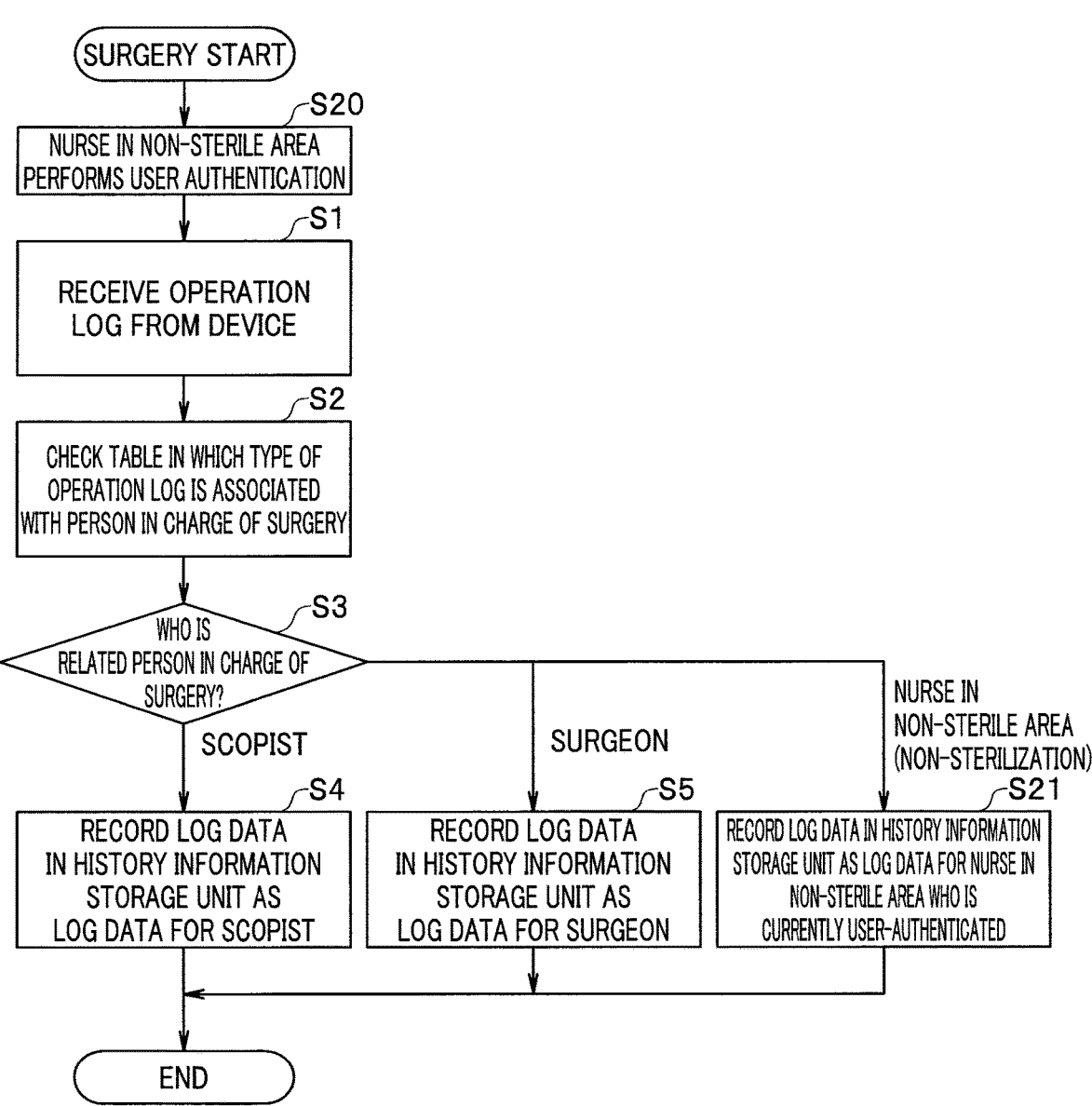
FIG. 12 is a flowchart illustrating an example of a flow of log data recording processing.

FIG. 12 is a flowchart illustrating an example of a flow of log data recording processing. Note that processes in FIG. 12 similar to the processes in FIG. 7 are assigned the same reference numerals and descriptions are omitted. It is assumed that the surgeon and the scopist have performed user authentication once prior to the processes in FIG. 12.

The nurse in the non-sterile area performs user authentication before the operation (S20). When the control unit 41 determines, as a result of the process in S3, that the related person in charge of surgery is a nurse in the non-sterile area, the control unit 41 records the log data in the history information storage unit 42*c* as log data for the nurse in the non-sterile area who is currently user-authenticated (S21) and ends the processing.

As for the person in charge of surgery in the non-sterile area where a plurality of persons in charge of surgery may possibly participate, the control unit 41 performs, through the above-described processing, user authentication and records the user authentication in association with the operation log at each operation, and can thereby easily extract operation logs for each person in charge of surgery who has performed the operation.

Third Embodiment

Next, a third embodiment will be described.

According to the third embodiment, a video seen from the line of sight of the person in charge of surgery is recorded for each person in charge of surgery so as to be displayed together with each operation log.

Figure 13:
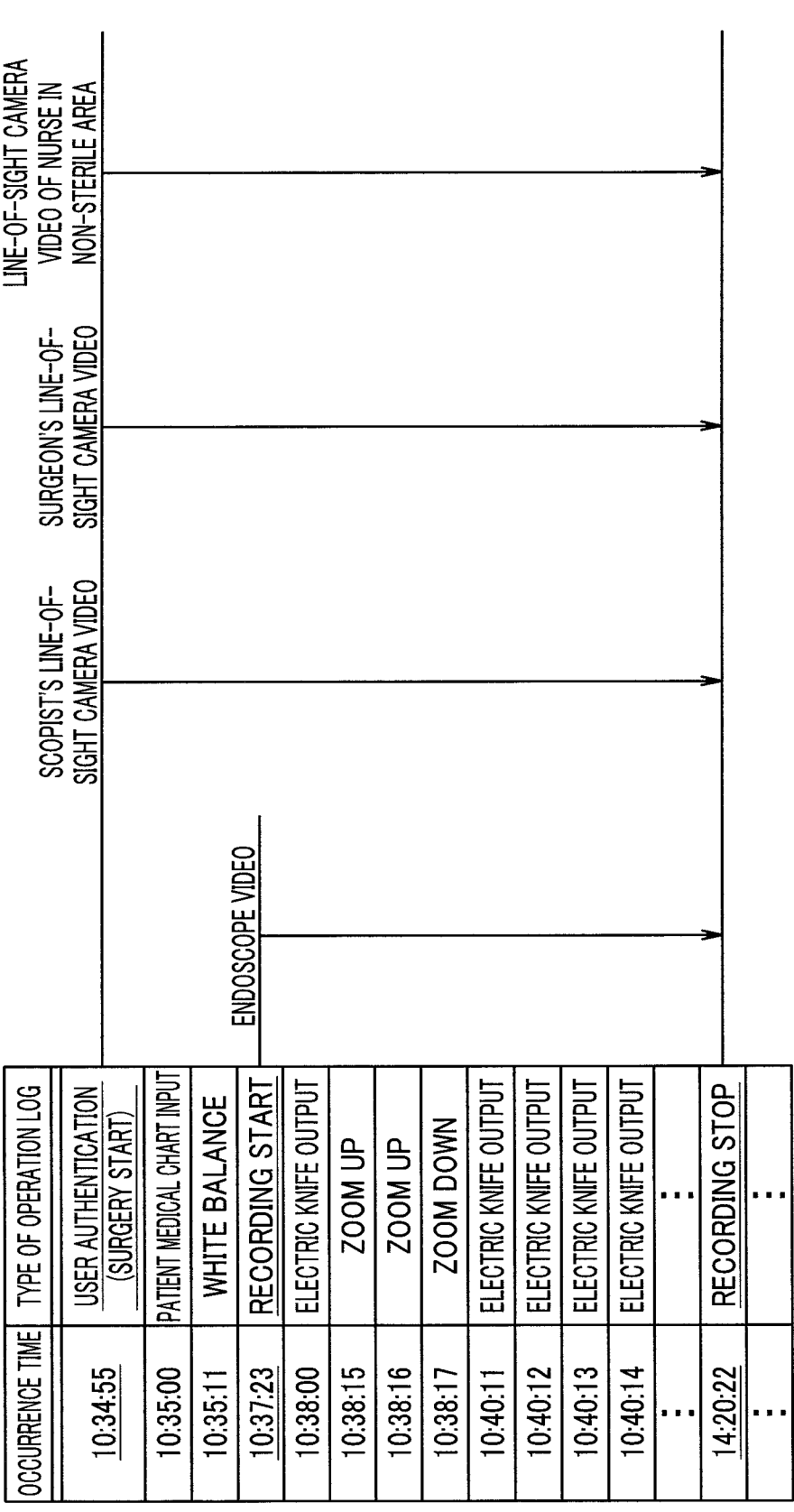
FIG. 13 is a diagram for describing recording start timing of a line-of-sight camera video.

FIG. 13 is a diagram for describing recording start timing of a line-of-sight camera video. Each person in charge of surgery wears glasses with camera or the like capable of recording a line-of-sight camera video. The glasses with camera are connected to the control unit 41 via the communication I/F 43. As shown in FIG. 13, the control unit 41 as a recording control unit starts recording the line-of-sight camera video of each person in charge of surgery at the start of surgery, that is, at the same time as user authentication. Furthermore, the control unit 41 as a recording control unit starts recording an endoscope video through a recording start operation. Note that the control unit 41 records the line-of-sight camera video and the endoscope video in the storage apparatus 42.

FIG. 14A is a diagram illustrating an example of a display screen when a person in charge of surgery extracts log data of a scopist, FIG. 14B is a diagram illustrating an example of a display screen when a person in charge of surgery extracts log data of a surgeon and FIG. 14C is a diagram illustrating an example of a display screen when a person in charge of surgery extracts log data of a nurse in a non-sterile area.

When the person in charge of surgery inputs information on the person in charge of surgery to be extracted using the operation panel apparatus 21, the control unit 41 as a display control unit displays the inputted log data related to the person in charge of surgery and a line-of-sight camera video and/or endoscope video.

When, for example, the person in charge of surgery is a scopist, as shown in FIG. 14A, the control unit 41 extracts and displays only operation logs related to the scopist from the log data stored in the history information storage unit 42*c*, and also displays a line-of-sight camera video of the scopist and an endoscope video together.

Similarly, when the person in charge of surgery is a surgeon, as shown in FIG. 14B, the control unit 41 displays only operation logs related to the surgeon from the log data stored in the history information storage unit 42*c*, and also displays a line-of-sight camera video of the surgeon and an endoscope video.

When the person in charge of surgery is a nurse in the non-sterile area, as shown in FIG. 14C, the control unit 41 displays only operation logs related to the nurse in the non-sterile area from the log data stored in the history information storage unit 42*c*, and also displays a line-of-sight camera video of the nurse in the non-sterile area.

When the person in charge of surgery is a scopist and a surgeon, the control unit 41 displays an endoscope video and each line-of-sight camera video, and when the person in charge of surgery is a nurse in the non-sterile area, the control unit 41 displays only a line-of-sight camera video. Thus, displaying operation logs and videos (endoscope video and/or line-of-sight camera video) for each person in charge of surgery makes it easier to identify trends and problems of the person in charge of surgery.

It is seen, for example, from 10:38:15 to 10:38:17 in FIG. 14A, that zoom UP and DOWN are repeated. Furthermore, it is seen by checking the endoscope video that zoom is flapping about. This allows the scopist to find a point for improvement of "making practice so as to achieve an appropriate zoom magnification with less operation."

It is seen from 10:40:11 to 10:40:13 in FIG. 14B that electric knife outputs are performed consecutively and the patient's burden is increasing. It is seen by checking the endoscope video that there is a lot of output time. This allows the surgeon to find a point for improvement of, for example, "taking care so as to disperse electric knife outputs a little more."

It is seen from 10:35:00 to 10:37:23 in FIG. 14C that patient medical chart input is performed, which takes two or more minutes. By checking a line-of-sight camera video, it is possible to find what is taking time. This allows the nurse in the non-sterile area to find a point for improvement of, for example, "considering a little more efficient input method."

FIG. 15 is a diagram illustrating an example in which log data and video for each person in charge of surgery obtained during surgery are compared with model log data and model video.

As shown in FIG. 15, the control unit 41 can acquire model log data and model video from the server/cloud 51, compare the model log data and model video with log data and video for each person in charge of surgery obtained during surgery this time and automatically generate a point for improvement. The model video is a model line-of-sight camera video and a model endoscope video of the scopist.

The control unit 41 compares the log data and video for each person in charge of surgery obtained during surgery this time with model logs acquired from the server/cloud 51 to thereby automatically generate a point for improvement of, for example. "taking time to adjust zooming." Furthermore, the control unit 41 compares the endoscope video for each person in charge of surgery obtained during surgery this time and the scopist's line-of-sight camera video with a model video acquired from the server/cloud 51, and can thereby visually transmit a point for improvement for each person in charge of surgery.

Figure 16:
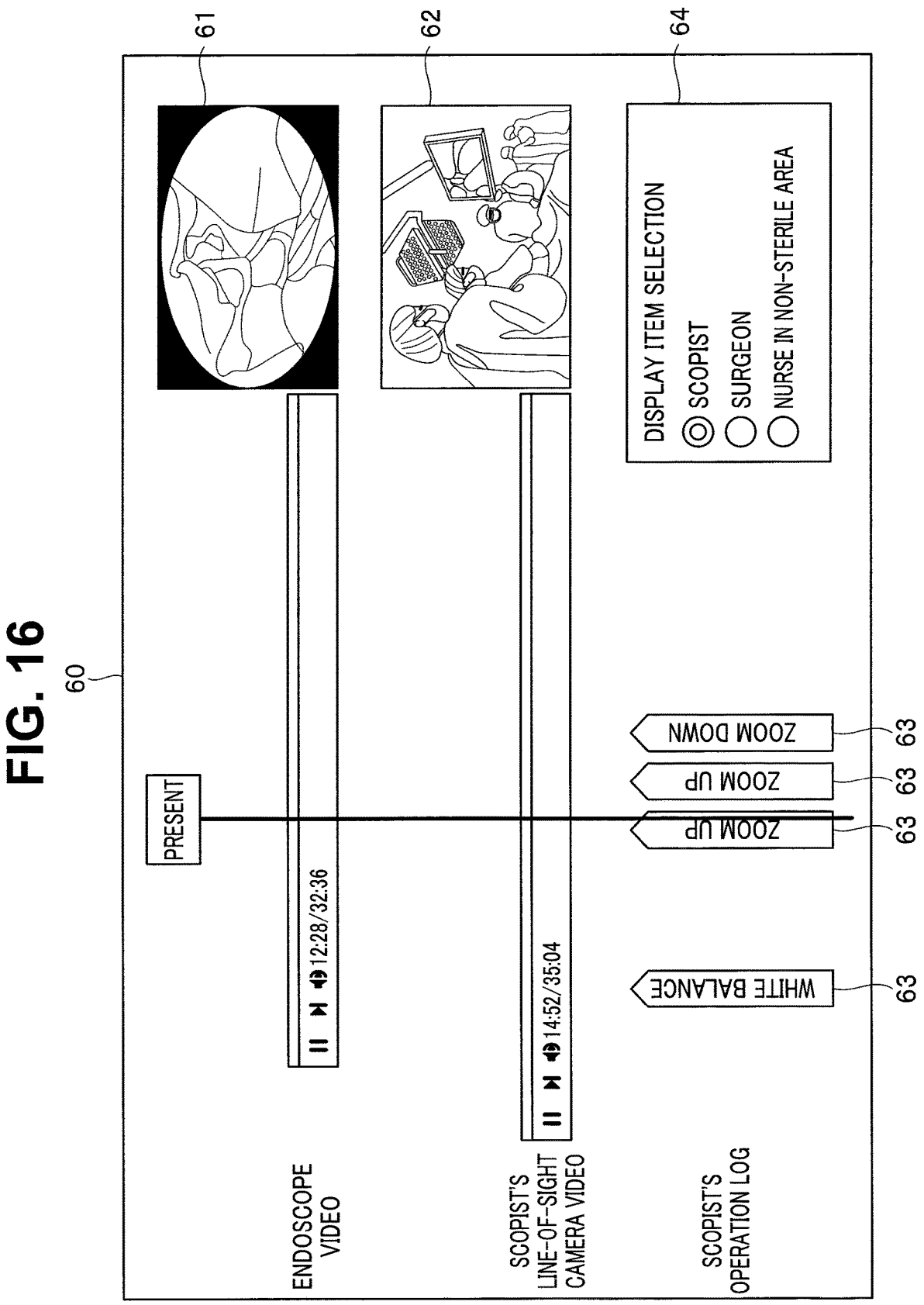
FIG. 16 is a diagram illustrating an example of a display screen that displays log data and video for each person in charge of surgery obtained during surgery.

FIG. 16 is a diagram illustrating an example of a display screen displaying log data and a video for each person in charge of surgery obtained during surgery.

A display screen 60 includes a display section 61 configured to display an endoscope video, a display section 62 configured to display a line-of-sight camera video, a plurality of operation logs 63, and a display item selection section 64. The screen generating program for displaying the display screen 60 is stored in the program storage unit 42*a*.

The person in charge of surgery can select a person in charge of surgery to be displayed on the display screen 60 using the display item selection section 64. In the example in FIG. 16, a scopist is selected, and so a line-of-sight camera video of the scopist and operation logs 63 of the scopist in addition to the endoscope video are displayed on the display screen 60. Note that when the display item selection section 64 selects a nurse in the non-sterile area, no endoscope video is displayed on the display section 61 and only the line-of-sight camera video of the nurse in the non-sterile area is displayed on the display section 62 as described above.

Playback of a line-of-sight camera video displayed on the display section 62 starts according to the time of user authentication of the operation log. On the other hand, playback of an endoscope video displayed on the display section 61 starts according to the recording start time of the operation log. This makes it possible to match the playback timings of the line-of-sight camera video and the endoscope video and the person in charge of surgery can simultaneously check the states of the line-of-sight camera video, the endoscope video and the operation log 63 at a certain point in time.

As described above, the control unit 41 displays the operation logs 63 for each person in charge of surgery and video (endoscope video and/or line-of-sight camera video) during operation. As a result, situations of the patient and the operating room are visually transmitted to the person in charge of surgery during the operation, allowing the person in charge of surgery to understand points for improvement more easily.

Note that order of execution of steps in the flowcharts of the present specification may be changed, a plurality of steps may be executed simultaneously or steps may be executed in a different order for each step execution as long as such changes or the like do not contradict the nature of the steps. The present invention is not limited to the aforementioned embodiments, but various changes, modifications or the like are possible to the extent that such changes, modifications or the like do not change the gist of the invention.

What is claimed is:

1. A control apparatus comprising:
one or more processors comprising hardware, the one or more processors being configured to:
store identity of each of a plurality of persons in charge of surgery including a surgeon, a scopist and a nurse in an operating room who perform control of one or more devices included in the operation system, in association with each type of operation logs outputted by the one or more devices;
receive a plurality of operation logs obtained during the surgery based on the control by the plurality of persons in charge of surgery in the operating room;
for each of the plurality of operation logs received, add the identity of one of the plurality of persons in charge of surgery in the operating room, associated with the type of the each of the operation logs received to the each of the operation logs as data logs;
determine the identity of a reference person of the plurality of persons in charge of surgery referring to the data logs;
based on the identity of the reference person determined, extract a part of the data logs having the identity of the reference person added, and display only data of the reference person in a time-series manner; and
present information to be improved by the reference person based on the part of the data logs extracted.

2. The control apparatus according to claim 1, wherein the one or more processors are configured to:
perform a comparison of the part of the data logs extracted with a model log; and
present the information to be improved by the reference person based on a result of the comparison.

3. The control apparatus according to claim 2, wherein the one or more processors are configured to acquire the model log from an external server or cloud.

4. The control apparatus according to claim 1, further comprising an authentication information input interface configured to receive authentication information of the reference person,
wherein the one or more processors are configured to determine the identity of the reference person based on the authentication information received.

5. The control apparatus according to claim 1,
wherein the one or more processors are configured to:
record line-of-sight camera videos for each of the plurality of persons in charge of surgery and an endoscope video obtained by one of the one or more devices; and
control a display to display the part of the data logs extracted having the identity of the reference person and at least one of the line-of-sight camera videos of the reference person and the endoscope video obtained by the one of the one or more devices controlled by the reference person.

6. The control apparatus according to claim 1, wherein the one or more processors are configured to generate the information to be improved by the reference person automatically.

7. A computer-implemented method comprising:
storing identity of each of a plurality of persons in charge of surgery including a surgeon, a scopist, and a nurse in an operating room who perform control of one or more devices included in an operation system in association with each type of operation logs outputted by the one or more devices;

receiving a plurality of operation logs obtained during the surgery based on the control by the plurality of persons in charge of surgery in the operating room;

for each of the plurality of operation logs received, adding the identity of one of the plurality of persons in charge of surgery in the operating room associated with the type of the each of the operation logs received to the each of the operation logs as data logs;

determining the identity of a reference person of the plurality of persons in charge of surgery referring to the data logs;

based on the identity of the reference person determined, extracting a part of the data logs having the identity of the reference person added, and displaying only data of the reference person in a time-series manner; and presenting information to be improved by the reference person based on the part of the data logs extracted.

8. The computer-implemented method according to claim 7, comprising:

performing a comparison of the part of the data logs extracted with a model log; and presenting the information to be improved by the reference person based on a result of the comparison.

9. The computer-implemented method according to claim 8, wherein the model log is acquired from an external server or cloud.

10. The computer-implemented method according to claim 7, comprising:

receiving, by an authentication information input interface, input of authentication information of the reference person; and determining the identity of the reference person based on the input of authentication information received.

11. The computer-implemented method according to claim 7, further comprising:

recording line-of-sight camera videos for each of the plurality of persons in charge of surgery and an endoscope video obtained by one of the one or more devices; and controlling a display to display the part of the data logs extracted having the identity of the reference person and at least one of the line-of-sight camera videos of the reference person and the endoscope video obtained by the one of the one or more devices controlled by the reference person.

12. A medical centralized control system comprising:

a plurality of devices; and a control apparatus comprising one or more processors comprising hardware, the one or more processors being configured to:

centrally control and communicate with the plurality of devices; store identity of each of a plurality of persons in charge of surgery including a surgeon, a scopist, and a nurse in an operating room who perform control of the plurality of devices in association with each types of operation logs outputted by the plurality of devices;

receive a plurality of operation logs obtained during the surgery based on the control by the plurality of persons in charge of surgery in the operating room;

for each of the plurality of operation logs received, add the identity of one of the plurality of persons in charge of surgery in the operating room associated with the type of the each of the operation logs to the each of the operation logs received to the each of operation logs as data logs;

determine the identity of a reference person of the plurality of persons in charge of surgery referring to the data logs;

based on the identity of the reference person determined, extract a part of the data logs having the identity of the reference person added, and display only data of the reference person in a time-series manner; and present information to be improved by the reference person based on the part of the data logs extracted.

13. The medical centralized control system according to claim 12, wherein the one or more processors are configured to:

perform a comparison of the part of the data logs extracted with a model log; and present the information to be improved by the reference person based on a result of the comparison.

14. The medical centralized control system according to claim 12, further comprising an authentication information input interface configured to receive authentication information of the reference person, wherein the one or more processors are configured to determine the identity of the reference person based on the authentication information received.

15. The medical centralized control system according to claim 12, wherein the one or more processors are configured to:

record a line-of-sight camera video for each of the plurality of persons in charge of surgery and an endoscope video obtained by one of the plurality of devices; and control a display to display the part of the data logs extracted having the identity of the reference person and at least one of the line-of-sight camera video of the reference person and the endoscope video obtained by the one of the plurality of devices controlled by the reference person.

* * * * *